(12) United States Patent
Choi et al.

(10) Patent No.: US 9,261,494 B2
(45) Date of Patent: Feb. 16, 2016

(54) BIOSENSOR CARTRIDGE

(75) Inventors: Youn Suk Choi, Yongin Si (KR); Hun Joo Lee, Hawseong-si (KR); Jae Phil Do, Seoul (KR); Soo Suk Lee, Suwon-si (KR); Yeol Ho Lee, Seoul (KR); Jung Nam Lee, Incheon (KR); Joon Hyung Lee, Yongin Si (KR); Kyung Yeong Han, Seoul (KR); Sang Kyu Kim, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 1088 days.

(21) Appl. No.: 13/270,499

(22) Filed: Oct. 11, 2011

(65) Prior Publication Data
US 2012/0178178 A1 Jul. 12, 2012

(30) Foreign Application Priority Data

Jan. 6, 2011 (KR) .................... 10-2011-0001337
Aug. 3, 2011 (KR) .................... 10-2011-0077364

(51) Int. Cl.
*G01N 1/18* (2006.01)
*G01N 21/00* (2006.01)
*G01N 27/00* (2006.01)
*G01N 33/48* (2006.01)
*G01N 33/49* (2006.01)
*G01N 21/77* (2006.01)

(52) U.S. Cl.
CPC .............. *G01N 33/491* (2013.01); *G01N 21/77* (2013.01); *Y10T 436/25375* (2015.01)

(58) Field of Classification Search
CPC ................. G01N 33/491; G01N 21/77; Y10T 436/25375
See application file for complete search history.

(56) References Cited

U.S. PATENT DOCUMENTS

| 2,491,656 | A | * | 12/1949 | Goldman ....................... 366/242 |
| 5,344,571 | A | * | 9/1994 | Mendershausen et al. ... 210/723 |
| 6,398,956 | B1 | * | 6/2002 | Coville et al. ............ 210/321.75 |
| 2005/0026301 | A1 | * | 2/2005 | Petithory ............ B01L 3/50273 436/180 |
| 2008/0218276 | A1 | | 9/2008 | Sundby |
| 2008/0257754 | A1 | * | 10/2008 | Pugia et al. ................... 205/792 |
| 2008/0292502 | A1 | * | 11/2008 | Kitawaki et al. ................. 422/72 |

FOREIGN PATENT DOCUMENTS

| KR | 10-2004-0004202 A | 1/2004 |
| KR | 10-2005-0098948 A | 10/2005 |
| KR | 10-2009-0049414 A | 5/2009 |

* cited by examiner

*Primary Examiner* — Christopher A Hixson
(74) *Attorney, Agent, or Firm* — Leydig, Voit & Mayer, Ltd.

(57) ABSTRACT

A biosensor cartridge includes a plasma separator, a plasma metering chamber, a mixer, and a biosensor.

18 Claims, 5 Drawing Sheets

BIOSENSOR CARTRIDGE

CROSS-REFERENCE TO RELATED APPLICATIONS

This application claims priority to Korean Patent Application No. 10-2011-0001337, filed on Jan. 6, 2011, and Korean Patent Application No. 10-2011-0077364, filed on Aug. 3, 2011, and all the benefits accruing therefrom under 35 U.S.C. §119, the contents of which in its entirety are herein incorporated by reference.

BACKGROUND

1. Field

Provided is a biosensor cartridge for automating a complex process of a biosensor for blood tests.

2. Description of the Related Art

A biosensor causes a change in an electrical or optical signal using a specific binding, reaction, etc. between a biological material, such as protein, deoxyribonucleic acid ("DNA"), viruses, bacteria, cells, and tissues, and a sensor surface, thereby quantitatively or qualitatively analyzing and testing biomolecules.

Detection of a biological material requires a complex process for processing, reaction, and analysis of a reagent. Although the process varies according to an analysis method and the type of the material, a biosensor generally detects a biological material through a complex combination of processes such as filtering, metering, mixing, transport, reaction, and washing. Thus, according to conventional art, detection of a biological material is manually performed in respective laboratories using a variety of equipment.

For this reason, simultaneous development of biosensor technology and fluid-processing technology for automating and standardizing a test process is very important for a low-cost and high-efficiency test. Active development of technology for performing a process, which is currently performed manually in a clinical laboratory, in an automated single platform is under way.

SUMMARY

Provided is a platform capable of accurately and rapidly implementing an overall process of detecting a biological material that has been manually performed.

Provided is a cartridge which reagent preprocessing and reaction process for biosensor-based analysis is automated using microfluidic control technology.

Provided is a system that has high accuracy and high efficiency while reducing analysis cost and time for detecting a biological material using a biosensor.

Provided is a disposable cartridge for automatically performing an overall blood-based biosensing process using microfluidic control technology.

Provided is a biosensor cartridge including a plasma separator, a plasma metering chamber, a mixer, and a biosensor.

The plasma separator separates plasma from blood. The plasma metering chamber measures and stores the plasma separated by the plasma separator. The mixer not only stores a reagent for detecting a specific biological material from the plasma, but also mixes the plasma discharged from the plasma metering chamber and the stored reagent. The mixed solution of the plasma and the reagent discharged from the mixer is injected into the biosensor, and the biosensor detects the specific biological material in the plasma.

The biosensor cartridge may further include a plasma overflow reservoir. The plasma overflow reservoir may store the plasma overflowed from the plasma metering chamber.

The biosensor cartridge may further include a fluidic valve. The fluidic valve may be in a fluid path between the mixer and the biosensor. The fluidic valve may be opened when the mixed solution from the mixer flows into the biosensor, and be closed when air pressure is applied.

The biosensor cartridge may further include an air-bubble remover. The air-bubble remover may be between the mixer and the biosensor, and may remove air bubbles from the mixed solution before the mixed solution is injected into the biosensor.

The biosensor cartridge may further include a washer reservoir. The washer reservoir may be connected to the air-bubble remover, and the washer reservoir stores a washing fluid for washing the biosensor. The washing fluid may pass through the air-bubble remover before being introduced to the biosensor.

The biosensor cartridge may further include a waste reservoir. The waste reservoir may be connected to a back end of the biosensor, and may store and discharge a waste liquid which is discharged from the biosensor.

The plasma separator may include a blood injector, a plasma separation filter, a pressurizing channel, a plasma guiding plate, and a plasma outlet. The blood may be injected into the blood injector. The plasma separation filter may be connected to a lower end of the blood injector, and may block corpuscles in the blood and only pass the plasma. The pressurizing channel may be connected to an upper end of the blood injector, and may apply air pressure to the blood in the blood injector. The plasma guiding plate may be at a lower end of the plasma separation filter, and may transport of the plasma passed through the plasma separation filter. The plasma outlet may be in the plasma guiding plate, and may discharge the plasma transported by the plasma guiding plate.

The plasma separator may further include a filter pressing post, which maintains the plasma separation filter and the plasma guiding plate in contact with each other. The plasma guiding plate includes a fine structure on a surface thereof facing the plasma separation filter. A fluid path is defined by the contacting plasma guiding plate having the fine structure and plasma separation filter, so that a capillary action is generated in the fluid path.

The plasma metering chamber may include a plasma storage, a plasma inlet, a plasma overflow outlet, an air inlet/outlet, and a plasma outlet. The plasma may be collected in the plasma storage. The plasma inlet may be connected to an upper end of the plasma storage, and the plasma separated by the plasma separator may flow therethrough into the plasma storage. The plasma storage has a certain volume capacity and where the stored plasma overflows the volume capacity of the plasma storage, the overflowed plasma may be discharged into the plasma overflow reservoir through the plasma overflow outlet. The air inlet/outlet may be connected to the upper end of the plasma overflow reservoir, and may discharge air from the plasma overflow reservoir while the plasma is collected in the plasma overflow reservoir and apply air pressure to the plasma after the plasma is collected in the plasma overflow reservoir. The plasma outlet may be connected to a lower end of the plasma storage, and the plasma in the plasma storage may be discharged therethrough.

A lower end of the plasma storage may have a throttle structure including a width which decreases in a direction toward the plasma outlet.

The mixer may include two or more chambers in which the plasma flowed from the plasma separator and the reagent for detecting a specific biological material from the plasma are stored, and in which the stored reagent and another reagent flowed from the outside are mixed. The mixer may include a reagent outlet discharging the reagent mixture, and a lower end of the mixer may have a throttle structure including a width which decreases in a direction toward the reagent outlet.

The biosensor may be a mass-based sensor. The biosensor may be one of a quartz crystal microbalance ("QCM"), a cantilever sensor, and a surface acoustic wave ("SAW") sensor.

The biosensor cartridge whose blood-based biological material detection and test process is automated as above may perform all processes from reagent preprocessing to final detection in a single equipment.

Also, the biosensor cartridge may enable low-cost and high-efficiency detection, and enable the accuracy of detection to be improved by preventing experimental errors caused in a conventional manual process.

The biosensor cartridge may be extensively applied to detection of biological materials based on various biosensors.

BRIEF DESCRIPTION OF THE DRAWINGS

The above and other aspects, advantages and features of this invention will become more apparent by describing in further detail exemplary embodiments thereof with reference to the accompanying drawings, in which.

DETAILED DESCRIPTION

Figure 1:
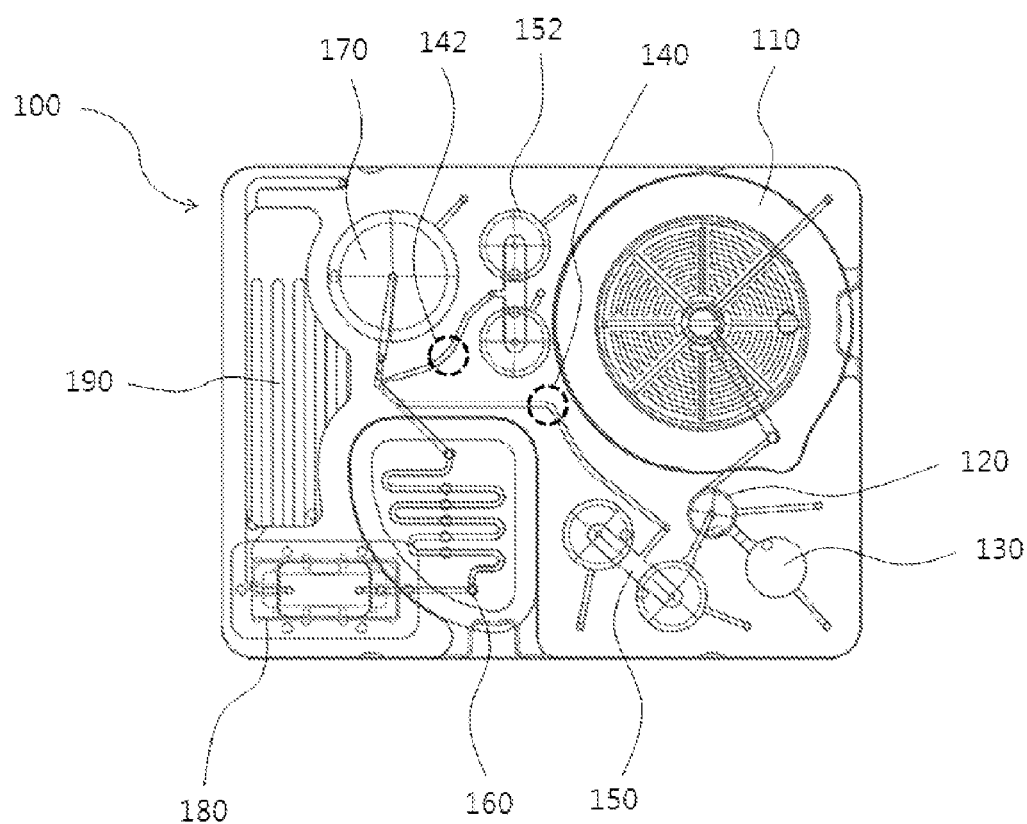
FIG. 1 is a top view of a biosensor cartridge, according to an exemplary embodiment of the present invention.

The invention now will be described more fully hereinafter with reference to the accompanying drawings, in which a non-limiting embodiment is shown. This invention may, however, be embodied in many different forms, and should not be construed as limited to the exemplary embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

One or more embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear portions. Moreover, sharp angles that are illustrated may be rounded. Thus, the regions illustrated in the figures are schematic in nature and their shapes are not intended to illustrate the precise shape of a region and are not intended to limit the scope of the claims.

FIG. 1 is a top view of a biosensor cartridge, according to an exemplary embodiment of the present invention.

Referring to FIG. 1, a biosensor cartridge 100 includes a plasma separator 110, a plasma metering chamber 120, a plasma overflow reservoir 130, fluidic valves 140 and 142, mixers 150 and 152, an air-bubble remover 160, a washer reservoir 170, a biosensor 180, and a waste reservoir 190. The variety of components introduced above for preprocessing and analyzing a reagent are entirely in the single cartridge 100. The respective components will be described in detail below.

The plasma separator 110 is a component for separating a biological component such as plasma from a biological sample such as blood. Plasma separation is performed by a capillary action or application of pressure. The plasma separator 110 may include two or more stacked filters to increase plasma separation efficiency in the limited area of the cartridge 100.

Figure 2:
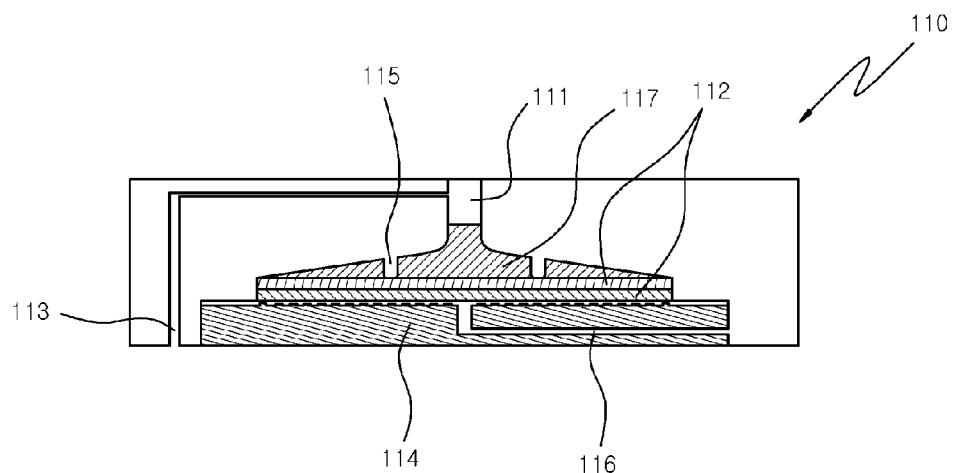
FIG. 2 is a cross-sectional view of a plasma separator of the biosensor cartridge shown in FIG. 1, according to an exemplary embodiment of the present invention.
Figure 3:
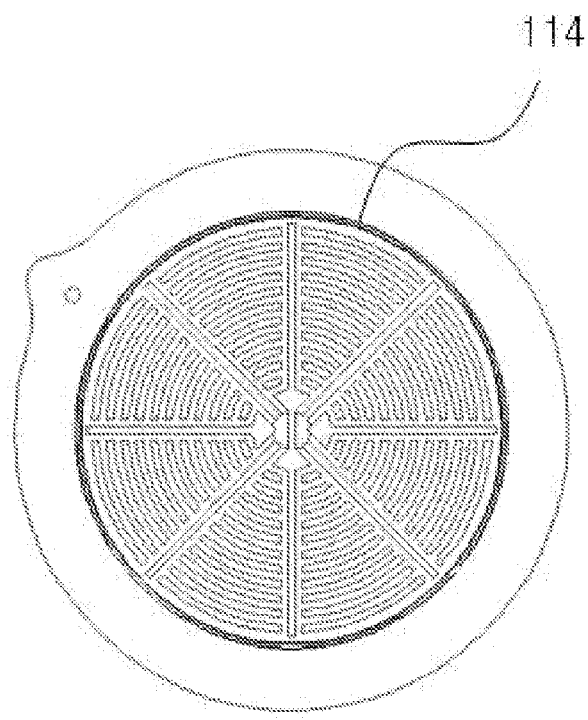
FIG. 3 is a top view of a plasma guiding plate of the plasma separator shown in FIG. 2, according to an exemplary embodiment of the present invention.

FIG. 2 is a cross-sectional view of a plasma separator of the biosensor cartridge shown in FIG. 1, according to an exemplary embodiment of the present invention, and FIG. 3 is a top view of a plasma guiding plate of the plasma separator shown in FIG. 2, according to an exemplary embodiment of the present invention. As shown in FIG. 2, the plasma separator 110 includes a blood injector 111, a plasma separation filter 112, a pressurizing channel 113, a plasma guiding plate 114, a filter pressing post 115, and a plasma outlet 116.

Blood 117 is injected into the plasma separator 110 through the blood injector 111. The plasma separation filter 112 is connected to a lower end of the blood injector 111 such that the plasma separation filter 112 is in fluid connection with the blood injector 111. The pressurizing channel 113 is connected to an upper end of the blood injector 111 such that the pressurizing channel 113 is in fluid connection with the blood injector 111. The blood 117 injected into the blood injector 111 passes through the plasma separation filter 112 by air pressure applied through the pressurizing channel 113.

The plasma separation filter 112 blocks corpuscles in the blood 117 and passes only plasma of the blood 117. As shown in the drawing, the plasma separation filter 112 may include two or more sub-filters or filter layers to increase plasma separation efficiency, or only one filter or filter layer may be used. The plasma guiding plate 114 is at a lower end of the plasma separation filter 112.

The plasma guiding plate 114 includes a fine structure for causing a capillary action. Referring to FIG. 3, the fine structure defines radial fluid paths on the plasma guiding plate 114. Since the plasma separation filter 112 and the plasma guiding plate 114 are closely adhered to each other by the filter pressing post 115, plasma passed through the plasma separation filter 112 gathers at a central fluid path of the plasma guiding plate 114 due to a capillary action caused in the fluid paths of the plasma guiding plate 114. The central fluid path of the plasma guiding plate 114 is in fluid connection with the plasma outlet 116 in the plasma guiding plate 114. The plasma from the plasma separation filter 112, guided by the plasma guiding plate 114 and transported through the plasma outlet 116 is discharged to the plasma metering chamber 120, which will be described later, along a fluid path.

The plasma separator 110 shown in FIGS. 2 and 3 corresponds merely to one exemplary embodiment, and is not limited to this structure. In the description above, the plasma separator 110 uses the capillary action of the fluid paths between the plasma separation filter 112 and the plasma guiding plate 114, as well as air pressure applied through the pressurizing channel 113. However, the plasma separator 110 according to another exemplary embodiment may only use the air pressure or the capillary action to perform plasma separation.

Figure 4A:
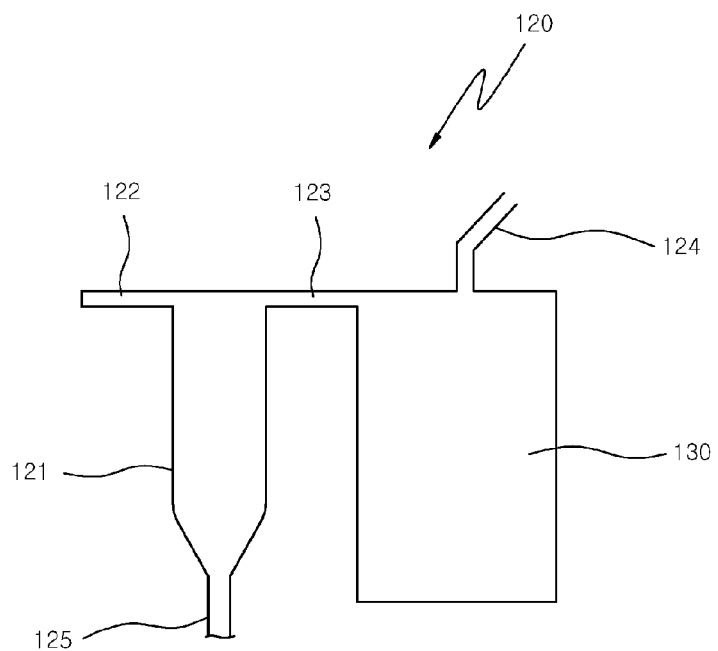
FIGS. 4A and 4B are cross-sectional views of a plasma metering chamber of the biosensor cartridge shown in FIG. 1, according to an exemplary embodiment of the present invention.
Figure 4B:
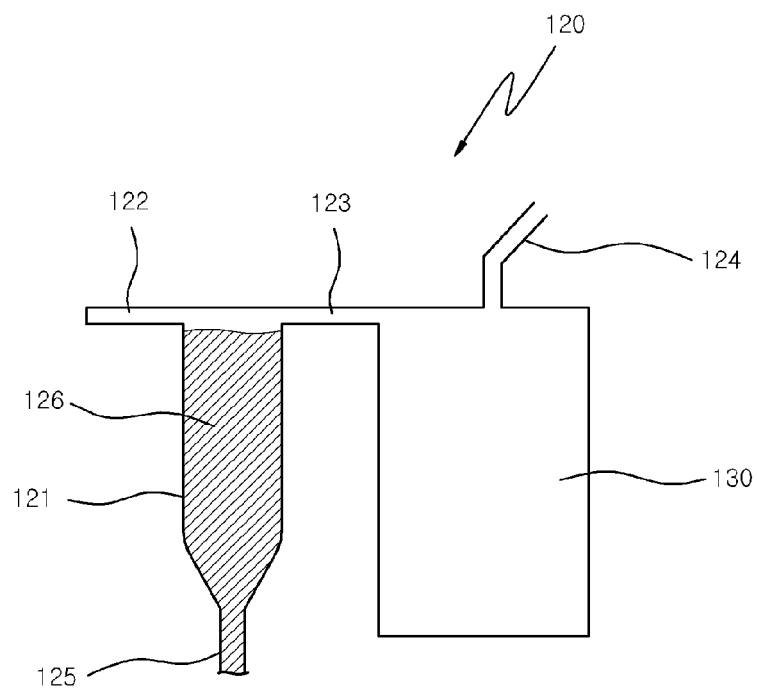

FIGS. 4A and 4B are cross-sectional views of a plasma metering chamber of the biosensor cartridge shown in FIG. 1, according to an exemplary embodiment of the present invention. As shown in FIGS. 4A and 4B, the plasma metering chamber 120 includes a plasma storage 121, a plasma inlet 122, a plasma overflow outlet 123, an air inlet/outlet 124, and a plasma outlet 125. The air inlet/outlet 124 may be considered as a portion of the plasma overflow reservoir 130, or the plasma overflow reservoir 130 may be considered as a portion of the plasma metering chamber 120.

The plasma separated by the plasma separator 110 is collected in the plasma metering chamber 120. The plasma metering chamber 120 is a component for measuring an amount or quantity of the separated plasma. The plasma metering chamber 120 has two functions. First, the plasma metering chamber 120 should reduce or effectively prevent plasma from leaking while the plasma is measured. For this reason, the lower end of the plasma metering chamber 120, specifically the plasma storage 121, has a throttle structure including a width which narrows toward the plasma outlet 125. Thus, although plasma 126 is collected in the plasma storage 121 as shown in FIG. 4B, the plasma 126 near the throttle structure cannot flow to and/or completely through the plasma outlet 125 due to surface tension. To maximize this effect, the throttle structure may be hydrophobic. While the plasma 126 is collected in the plasma storage 121, air in the plasma storage 121 may be discharged to outside the plasma storage 121 through the air inlet/outlet 124, and thus inflow of the plasma 126 does not increase the pressure in the plasma storage 121. In this way, the above-mentioned first function of the plasma metering chamber 120 may be achieved. In other words, while the plasma 126 is separated and collected, the plasma 126 does not leak from the plasma metering chamber 120 to the mixer 150.

Second, the plasma metering chamber 120 should measure the certain amount of plasma. The plasma measurement is determined based on a volume of the metering chamber 120, such as a volume of the plasma storage 121. After the plasma 126 flowed from the plasma separator 110 completely fills the volume of the metering chamber 120, for example, the plasma storage 121, overflow plasma is discharged into the plasma overflow reservoir 130 through the plasma overflow outlet 123. Even though a large quantity of plasma may be delivered from the plasma separator 110, all the plasma over and above the certain volume is flowed into the plasma overflow reservoir 130 so that only the plasma needed is measured in the plasma metering chamber 120.

The plasma storage 121 has a similar shape to a syringe. The upper end of the plasma storage 121 is in fluid connection to the plasma inlet 122 and the plasma overflow outlet 123, and a lower end is in fluid connection to the plasma outlet 125. In the above plasma separator 110, separated plasma 126 is collected in the plasma storage 121 after passing through the plasma inlet 122. Subsequently, when air pressure is applied through the air inlet/outlet 124 to the plasma storage 121, the plasma 126 in the plasma storage 121 is discharged through the plasma outlet 125.

As described above, the throttle structure of the plasma metering chamber 120 corresponds merely to one exemplary embodiment, and is not limited to this structure. The plasma metering chamber 120 according to another exemplary embodiment may employ a valve to prevent or enable discharge of the plasma 126 from the plasma metering chamber 120 to the mixer 150. Also, the air inlet/outlet 124 and the throttle structure of the plasma metering chamber 120 can be applied to the mixers 150 and 152, which will be described later, in the same way to reduce or effectively prevent a reagent from being abnormally discharged.

The fluidic valves 140 and 142 are optional components in a fluid path between the mixer 150 and the biosensor 180, and prevent or enable flow of a fluid in the fluid path. In an exemplary embodiment, for example, the fluidic valve 140 is opened when the mixture solution formed in the mixer 150 is flowed into the biosensor 180, and is closed when air pressure is applied, if the solution should otherwise not flow. In other words, when air pressure is applied to discharge the reagent collected in the mixer 150 to the biosensor 180, the fluidic valve 140 blocks the fluid path between the mixer 150 and the biosensor 180, to reduce or effectively prevent the loss of air pressure.

The mixers 150 and 152 are components for storing a reagent for analysis, and for mixing the plasma 126 flowed from the plasma metering chamber 120 and the reagent. In an exemplary embodiment, for example, among the mixers 150 and 152, for convenience, the mixer 150 paired with the plasma metering chamber 120 is referred to as a first mixer, and the other mixer 152 is referred to as a second mixer. As mentioned above, the biosensor cartridge 100 includes the two mixers 150 and 152, but is not limited to this constitution. In another exemplary embodiment, the biosensor cartridge may include only the first mixer 150. According to circumstances, three or more mixers may be included.

The first mixer 150 stores a specific reagent used to detect a biological material, and mixes the plasma flowed from the plasma metering chamber 120 and the reagent. When the biosensor cartridge 100 is used to detect a biological material such as protein in blood, an adsorbent for adsorbing the protein in blood is stored in the first mixer 150 as a reagent. In one exemplary embodiment, for example, gold nanoparticles can be used as an adsorbent. Various reagents may be stored in the first mixer 150, and the reagent stored in the first mixer 150 varies according to a biological material that the biosensor cartridge 100 is used to detect.

The second mixer 152 stores an additional reagent for improving sensitivity for biological material detection. In an exemplary embodiment, for example, when gold nanoparticles for adsorbing protein are stored in the first mixer 150 of the biosensor cartridge 100, a reagent capable of improving sensitivity by increasing the mass of the gold nanoparticles is stored in the second mixer 152. For example, $HAuCl_4$ as a gold source or $NH_2OH \cdot HCl/H_2O$ as a reducing agent may be stored in the second mixer 152. Due to these reagents, the gold nanoparticles are electroless-plated, and the particle size increases. Various reagents may be stored in the second mixer 152, and reagents stored in second mixer 152 vary according to a biological material that the biosensor cartridge 100 is used to detect. Also, according to the type of the reagent, the second mixer 152 alone or more mixers may be used. Further, when improvement in sensitivity is not as important, the second mixer 152 may be omitted.

As described for the plasma metering chamber 120 above, the respective mixers 150 and 152 can have the same structure as the plasma metering chamber 120 which has the air inlet/outlet 124 and the throttle structure to prevent a reagent from being abnormally discharged to the biosensor 180. In an exemplary embodiment illustrated in FIG. 5, the mixer 150 includes multiple chambers each having the throttle structure where a width narrows toward an outlet thereof. Also, like the plasma metering chamber 120, the mixers 150 and 152 may employ a valve for preventing or enabling discharge of the plasma.

Figure 5:
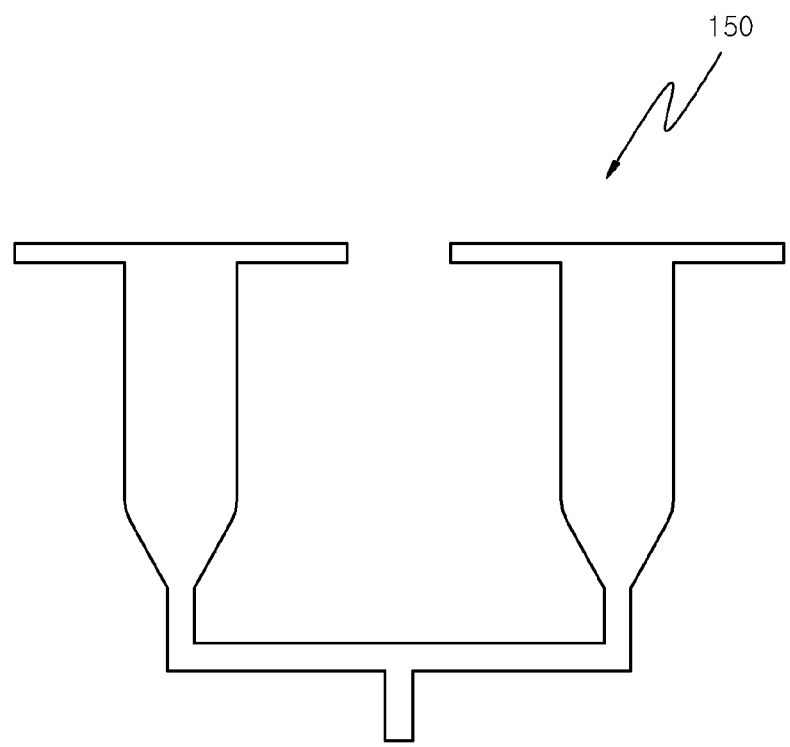
FIG. 5 is a cross-sectional view of a mixer of the biosensor cartridge shown in FIG. 1, according to an exemplary embodiment of the present invention.

The mixer 150 is a component for mixing reagents as well as for storing plasma, and is in direct fluid connection with the plasma metering chamber 120. The mixer 150 may include two or more chamber. In one exemplary embodiment, for example, the mixer 150 includes two chambers, as shown in FIG. 5. The reagent is stored in both of the two chambers, or the reagent is stored in only one chamber and another plasma flowing from outside the mixer 150 is stored in the other chamber. While the mixer 150 operates, the reagent is contained in both of the two chambers, and if negative pressure and positive pressure is applied in turn by using air pressure, the reagent in each chamber moves reciprocally along the fluid path to be mixed. Here, an outlet of the mixer 150 is in the intermediate position of the fluid path between the chambers, and because the dimension of the outlet is smaller than that of the fluid path between the chambers, the fluid does not leak out of the mixer 150 due to surface tension while mixing in the mixer 150.

The mixers 150 and 152 are in fluid connection to the air-bubble remover 160. The air-bubble remover 160 is a component for removing air bubbles which are introduced from outside the biosensor cartridge 100 or generated within the biosensor cartridge 100, and consists of a hydrophobic membrane. Since a sensing result significantly varies according to whether or not a reagent mixture solution injected from the mixers 150 and 152 into the biosensor 180 contains air, the air-bubble remover 160 is used to remove noise caused by air bubbles. While the reagent mixture solution discharged from the mixers 150 and 152 is passed through the air-bubble remover 160, air bubbles are discharged to the outside through a channel surface adjoining the hydrophobic membrane, and only a fluid without the air bubbles for sensing is injected into the biosensor 180.

The washer reservoir 170 is also in fluid connection to the air-bubble remover 160. The washer reservoir 170 is a component for storing a washing fluid for washing the biosensor 180. The washing fluid flowed from the washer reservoir 170 passes through the air-bubble remover 160 and then is injected into the biosensor 180.

The biosensor 180 causes a change in an electrical or optical signal using a specific binding, reaction, etc. between a biological material and a sensor surface, thereby quantitatively or qualitatively analyzing and testing the material. A front end of the biosensor 180 is in fluid connection with the mixers 150 and 152 and the washer reservoir 170 through the air-bubble remover 160, and a back end is in fluid connection with the waste reservoir 190. The waste reservoir 190 is a component for storing and discharging all waste liquid that has been completely sensed by the biosensor 180.

The biosensor 180 is one of a mass-based sensor, an optical sensor, and an electrical sensor. As the mass-based sensor, a quartz crystal microbalance ("QCM"), cantilever sensor, surface acoustic wave ("SAW") sensor, and the like may be used. As the optical sensor, sensors using ultraviolet ("UV")-visible spectrometry, colorimetry, surface plasmon resonance ("SPR"), fluorescence, and the like may be used. As the electrical sensor, an electrochemistry sensor, a field effect transistor ("FET") sensor, and the like may be used.

The biosensor 180 disclosed herein employs a SAW sensor, which is a mass-based sensor. A SAW is an elastic wave traveling along the surface of a piezoelectric material, and is used in a biosensor that senses a gene or protein through the principle that strong interaction between the biosensor and an adjoining medium has a strong influence on the velocity and amplitude of an elastic wave. The biosensor 180 includes four SAW sensors. In the illustrated exemplary embodiment, three-types of proteins (troponin I, creatine kinase-myocardial band ("CK-MB"), and myoglobin) are detected from blood. Thus, the biosensor 180 includes three SAW sensors for detecting the respective proteins and one reference SAW sensor for comparison. Like the biosensor 180 that is not limited to a specific type of sensor, the number of sensors is not limited.

Thus far, the constitution of the biosensor cartridge 100 has been described in detail. An exemplary embodiment of a process of detecting a biological material using the biosensor cartridge 100 will be described below.

Blood is injected into the plasma separator 110, and plasma separated from the blood is collected in the plasma metering chamber 120. Reagents are previously stored in the first mixer 150 and the second mixer 152, respectively. Here, it will be attempted to detect three kinds of proteins from the blood. Thus, gold nanoparticles are stored in the first mixer 150 as an absorbent for absorbing protein in plasma, a gold source for improving sensitivity by increasing the mass of the gold nanoparticles and/or a reducing agent is stored in the second mixer 152.

When the plasma is collected in the plasma metering chamber 120, air pressure is applied to the fluidic valve 140, the plasma metering chamber 120, and the first mixer 150. Then, the fluidic valve 140 is closed, and the plasma in the plasma metering chamber 120 is injected into the first mixer 150 containing the gold nanoparticles. The plasma and gold nanoparticles supplied to the mixer 150 are mixed while flowing through a fluid path of the mixer 150, and protein in the plasma is absorbed into the gold nanoparticles.

While the reagent mixture solution discharged from the mixer 150 is passed through the air-bubble remover 160, air bubbles are removed, and the resultant reagent mixture solution is injected into the biosensor 180. The biosensor 180 is coated with a tagging material that reacts to a specific protein. Thus, when the reagent mixture solution is passed through the biosensor 180, the protein absorbed into the gold nanoparticles reacts to the tagging material and is attached to a sensor surface, and a change in mass is sensed. Here, the mass of the gold nanoparticles is too small to be sensed, and thus a follow-up process is performed to improve sensitivity.

In the follow-up process, a washing fluid is injected through the washer reservoir 170 to remove air bubbles from the air-bubble remover 160. Then, the washing fluid is injected into the biosensor 180 to wash the biosensor 180. In the washing process, gold nanoparticles abnormally remaining on the sensor surface other than gold nanoparticles normally bound to the sensor surface, are removed. Through this washing process, the accuracy of detection can be improved. The reagent mixture solution not bound to the sensor surface and the washing fluid are stored or discharged through the waste reservoir 190.

Subsequently, in the follow-up process, when air pressure is applied to the second mixer 152, the gold source and/or the reducing agent in the second mixer 152 are injected into the biosensor 180. When the reagent mixture solution discharged from the mixers 150 and 152 is passed through the air-bubble remover 160, air bubbles are removed, and the resultant reagent mixture solution is injected into the biosensor 180. While the reagent mixture solution in which the gold source and the reducing agent are mixed undergoes an oxidation-reduction reaction with the gold nanoparticles bound to the sensor surface, the mass of the gold nanoparticles increases, and thus a detection signal of the biosensor 180 is amplified. Finally, the biosensor 180 is washed again and performs sensing.

Figure 6:
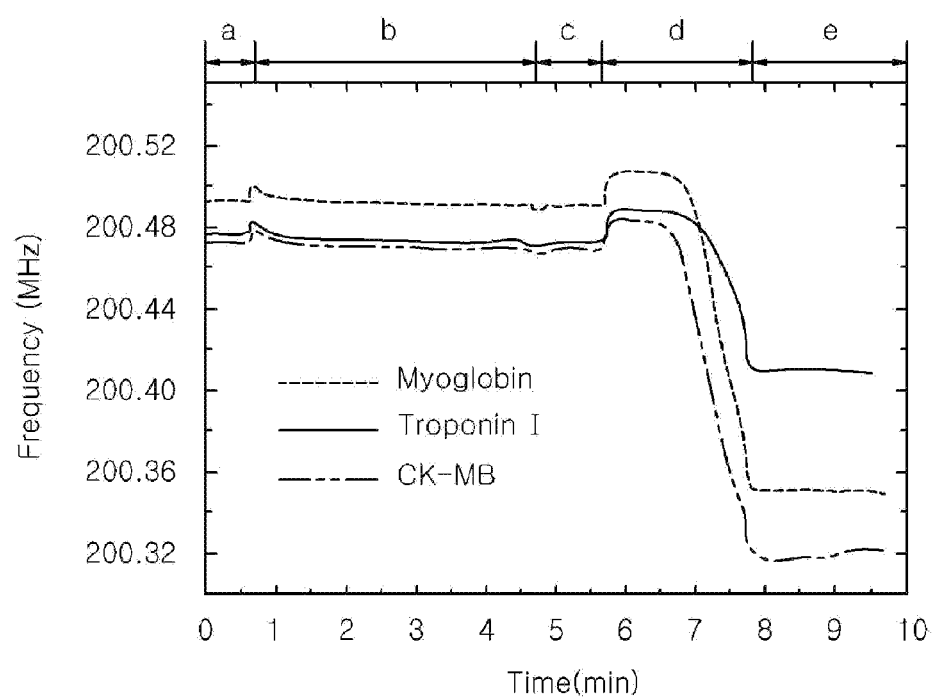
FIG. 6 is a graph showing sensing results obtained from the biosensor cartridge shown in FIG. 1 (x axis is time (minute, min), y axis is a frequency (megahertz, MHz)).

FIG. 6 is a graph showing sensing results obtained from the biosensor cartridge shown in FIG. 1. FIG. 6 shows results obtained by measuring a change in frequency in megahertz (MHz) over time in minutes (min), after injecting human blood spiked with 50 nanograms per milliliter (ng/ml) troponin I, 500 ng/ml CK-MB, and 1000 ng/ml myoglobin to the biosensor cartridge 100.

In FIG. 6, 'a' represents a plasma separation step, 'b' represents a sensor surface reaction step, 'c' represents a washing step, 'd' represents a signal amplification reaction step, and 'e' represents a final washing/sensing step. As can bee seen from FIG. 6, a change in frequency is small in the sensor surface reaction step 'b', but remarkable in an additional reaction process based on an increase in mass, that is, the signal amplification reaction step 'd'.

While the invention has been particularly shown and described with reference to embodiments thereof, it will be understood by those of ordinary skill in the art that various changes in form and details may be made therein without departing from the spirit or scope of the present invention as defined by the following claims

What is claimed is:

1. A biosensor cartridge, comprising:
   a plasma separator which separates plasma from blood;
   a plasma metering chamber which measures a quantity of and stores the plasma separated by the plasma separator, wherein a lower end of the plasma metering chamber has a throttle structure including a width which narrows toward a plasma outlet of the plasma metering chamber;
   a plasma overflow reservoir which is in fluid connection with the plasma metering chamber, wherein the plasma overflow reservoir stores the plasma which overflows from the plasma metering chamber;
   an air inlet/outlet which is directly connected to an upper end of the plasma overflow reservoir, wherein the air inlet/outlet discharges air from the plasma metering chamber while the plasma collects in the plasma metering chamber and applies air pressure to the plasma metering chamber after the collected plasma is in the plasma metering chamber;
   a mixer which stores a reagent which is used in detecting a specific biological material of the plasma, and mixes the plasma which is discharged from the plasma metering chamber and the stored reagent; and
   a biosensor into which the mixed solution of the plasma and the reagent which is discharged from the mixer is injected, wherein the biosensor detects the specific biological material in the plasma.

2. The biosensor cartridge according to claim 1, further comprising a fluidic valve which is in a fluid path between the mixer and the biosensor, wherein the fluidic valve is configured to open to permit the flow of the mixed solution from the mixer into the biosensor and configured to close when air pressure is applied to the mixer.

3. The biosensor cartridge according to claim 1, further comprising two or more mixers, wherein the two or more mixers store different reagents.

4. The biosensor cartridge according to claim 1, wherein the mixer comprises:
   two or more chambers which each store a reagent, and
   a fluid path through which the reagent in each chamber moves between the chambers.

5. The biosensor cartridge according to claim 1, further comprising an air-bubble remover which is between the mixer and the biosensor, wherein the air-bubble remover removes air bubbles from the mixed solution before the mixed solution is injected into the biosensor.

6. The biosensor cartridge according to claim 1, further comprising a washer reservoir which is between the mixer and the biosensor, and through which a washing fluid is injected into the biosensor.

7. The biosensor cartridge according to claim 1, further comprising a waste reservoir which is in fluid connection to an end of the biosensor, wherein the waste reservoir stores and discharges a waste liquid which is discharged from the biosensor.

8. The biosensor cartridge according to claim 1, wherein the plasma separator comprises:
a blood injector into which the blood is injected;
a plasma separation filter which is in fluid connection to a lower end of the blood injector, wherein the plasma separation filter blocks corpuscles in the blood and only passes the plasma;
a pressurizing channel which is in fluid connection to an upper end of the blood injector opposite to the lower end, wherein the pressurizing channel applies air pressure to the blood in the blood injector; and
a plasma guiding plate which is at a lower end of the plasma separation filter, wherein the plasma guiding plate transports the plasma which has passed through the plasma separation filter and includes a plasma outlet within the plasma guiding plate, and through which the transported plasma from the plasma guiding plate is discharged.

9. The biosensor cartridge according to claim 8, wherein the plasma separator further comprises a filter pressing post which maintains contact of the plasma separation filter and the plasma guiding plate to each other,
the plasma guiding plate further includes a fine structure on a surface thereof facing the plasma separation filter, and
a fluid path is defined by the contacting plasma separation filter and the plasma guiding plate including the fine structure, so that a capillary action is generated by the fluid path.

10. The biosensor cartridge according to claim 1, wherein the plasma metering chamber comprises:
a plasma storage in which the plasma is collected;
a plasma inlet which is in fluid connection to an upper end of the plasma storage, and through which the plasma separated by the plasma separator flows to the plasma storage; and
the plasma outlet which is in fluid connection to a lower end of the plasma storage, and through which the plasma in the plasma storage is discharged.

11. The biosensor cartridge according to claim 1, wherein the biosensor includes one of a mass-based sensor, an optical sensor, and an electrical sensor.

12. The biosensor cartridge according to claim 1, wherein the biosensor includes one of a quartz crystal microbalance, a cantilever sensor, and a surface acoustic wave sensor.

13. The biosensor cartridge of claim 1, further comprising
a fluidic valve which is in a fluid path between the mixer and the biosensor, wherein the fluid valve opens when the mixed solution flows from the mixer into the biosensor and closes when air pressure is applied to the mixer;
an air-bubble remover which is between the mixer and the biosensor, wherein the air-bubble remover removes air bubbles from the mixed solution before the mixed solution is injected into the biosensor;
a washer reservoir which is in fluid connection to the air-bubble remover, and in which a washing fluid used in washing the biosensor is stored; and
a waste reservoir which is in fluid connection to an end of the biosensor, wherein the waste reservoir stores and discharges a waste liquid which is discharged from the biosensor.

14. The biosensor cartridge according to claim 1, wherein the plasma separator, the plasma metering chamber, the mixer and the biosensor are completely within the biosensor cartridge.

15. The biosensor cartridge according to claim 1, further comprising a flow path which is in fluid connection with the plasma separator, the plasma metering chamber, the mixer and the biosensor, wherein the flow path is completely within the biosensor cartridge.

16. A biosensor cartridge comprising:
a plasma separator which separates plasma from blood;
a plasma metering chamber which measures a quantity of and stores the plasma separated by the plasma separator, wherein a lower end of the plasma metering chamber has a throttle structure including a width which narrows toward a plasma outlet of the plasma metering chamber;
a plasma overflow reservoir which is in fluid connection with the plasma metering chamber, wherein the plasma overflow reservoir stores the plasma which overflows from the plasma metering chamber;
an air inlet/outlet which is in fluid connection to an upper end of the plasma overflow reservoir, wherein the air inlet/outlet discharges air from the plasma metering chamber while the plasma collects in the plasma metering chamber and applies air pressure to the plasma metering chamber after the collected plasma is in the plasma metering chamber;
a mixer which stores a reagent which is used in detecting a specific biological material of the plasma, and mixes the plasma which is discharged from the plasma metering chamber and the stored reagent; and
a biosensor into which the mixed solution of the plasma and the reagent which is discharged from the mixer is injected, wherein the biosensor detects the specific biological material in the plasma;
wherein the mixer comprises:
an air inlet/outlet through which air pressure is applied to the stored reagent; and
a reagent outlet through which the reagent is discharged,
wherein a lower end of the mixer has a throttle structure including a width which decreases in a direction toward the reagent outlet.

17. A biosensor cartridge, comprising:
a plasma separator which separates plasma from blood;
a plasma metering chamber which measures a quantity of and stores the plasma separated by the plasma separator, wherein a lower end of the plasma metering chamber has a throttle structure including a width which narrows toward a plasma outlet of the plasma metering chamber;
a plasma overflow reservoir which is in fluid connection with the plasma metering chamber, wherein the plasma overflow reservoir stores the plasma which overflows from the plasma metering chamber;
an air inlet/outlet which is in fluid connection to an upper end of the plasma overflow reservoir, wherein the air inlet/outlet discharges air from the plasma metering chamber while the plasma collects in the plasma metering chamber and applies air pressure to the plasma metering chamber after the collected plasma is in the plasma metering chamber;
a mixer which stores a reagent which is used in detecting a specific biological material of the plasma, and mixes the plasma which is discharged from the plasma metering chamber and the stored reagent; and
a biosensor into which the mixed solution of the plasma and the reagent which is discharged from the mixer is injected, wherein the biosensor detects the specific biological material in the plasma, wherein the biosensor includes one of a quartz crystal microbalance, a cantilever sensor, and a surface acoustic wave sensor.

18. The biosensor cartridge of claim 10, wherein the plasma storage is syringe-shaped, wherein a lower end of the plasma storage has a throttle structure including a width which narrows toward a plasma outlet of the plasma metering chamber.

* * * * *